United States Patent [19]

Djuric et al.

[11] Patent Number: 5,112,864

[45] Date of Patent: May 12, 1992

[54] PLA₂ INHIBITORS AS ANTIINFLAMMATORIES

[75] Inventors: Stevan W. Djuric, Glenview; Stephen H. Docter, Mt. Prospect; Richard A. Haack, Chicago, all of Ill.

[73] Assignee: G. D. Searle & Co., Chicago, Ill.

[21] Appl. No.: 707,529

[22] Filed: May 30, 1991

[51] Int. Cl.⁵ ............... A61K 31/235; A61K 31/38; C07C 69/78; C07D 333/32
[52] U.S. Cl. .................... 514/549; 514/448; 514/461; 514/543; 514/568; 514/570; 549/71; 549/499; 549/501; 560/51; 560/53; 562/549; 562/463; 562/464
[58] Field of Search ............... 549/71, 499, 501, 76, 549/77, 498, 502; 560/51, 53; 562/459, 463, 464; 514/544, 568, 570, 448, 461

[56] References Cited

U.S. PATENT DOCUMENTS

| | | | |
|---|---|---|---|
| 3,255,241 | 6/1966 | Schultz et al. | 260/516 |
| 3,912,656 | 10/1975 | Andrews et al. | 252/431 |
| 3,919,250 | 11/1975 | Pauling et al. | 260/340 |
| 4,015,010 | 3/1977 | Houlihan et al. | 424/308 |
| 4,469,885 | 9/1984 | Djuric et al. | 562/459 |

FOREIGN PATENT DOCUMENTS

| | | |
|---|---|---|
| 142145 | 5/1985 | European Pat. Off. |
| 282898 | 9/1988 | European Pat. Off. |
| 1457025 | 12/1976 | United Kingdom |

Primary Examiner—Glennon H. Hollrah
Assistant Examiner—Mark W. Russell
Attorney, Agent, or Firm—Cynthia S. Kovacevic; Paul D. Matukaitis; Roger A. Williams

[57] ABSTRACT

This invention relates to novel compounds for treating inflammatory conditions by inhibition of phospholipase A₂ activity of the formula

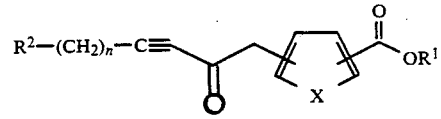

wherein X is oxygen, sulfur or —CH=CH—;
wherein R¹ is hydrogen, alkyl of 1 to 6 carbons or a pharmaceutically acceptable cation;
wherein R² is phenoxy, alkoxy, methyl, trifluoromethyl or phenyl;
wherein n is an integer from 1 to 20;

compositions comprised of the novel compounds; and methods of treating inflammatory conditions with these compositions.

21 Claims, No Drawings

PLA₂ INHIBITORS AS ANTIINFLAMMATORIES

BACKGROUND OF THE INVENTION

1. Field of the Invention

The present invention relates to pharmaceutical agents (compounds) which act as leukotriene B4 (LTB4) synthesis inhibitors in mammals. The compounds inhibit LTB4 synthesis by inhibiting phospholipase A2 (PLA₂) activity. PLA₂ is an important enzyme in the biosynthesis of leukotrienes as PLA₂ acts to release arachidonic acid from phospholipids. Once released, arachidonic acid is rapidly metabolized by a variety of enzymes of the arachidonic acid cascade to produce prostaglandins, leukotrienes and related compounds. The use of the compounds herein to inhibit PLA₂ activity thus inhibits the release of arachidonic acid from phospholipids. The inhibition of release of arachidonic acid similarly diminishes subsequent products in the arachidonic acid cascade, such as prostaglandins, leukotrienes, and related compounds, including LTB4.

LTB4 is an arachidonic acid metabolite which is produced by the 5-lipoxygenase pathway. Pharmacologically, LTB4 is an important mediator of inflammation. LTB4 is known to induce chemotaxis, chemokinesis, aggregation, and degranulation of leukocytes in vitro, and to induce accumulation of polymorphonuclear leukocytes, and increase vascular permeability and edema formation in vivo. Particularly high levels of LTB4 are detected in lesions in inflammatory diseases such as rheumatoid or spondylarthritis, gout, psoriasis, ulcerative colitis, Crohn's disease, multiple sclerosis and some respiratory diseases. Since the compounds herein inhibit PLA₂ and thereby LTB4 synthesis, the compounds of the present invention are useful in treating inflammatory conditions in mammals such as rheumatoid arthritis, inflammatory bowel disease, psoriasis and the like.

Accordingly, it is an object of this invention to produce compounds for use as pharmaceutical agents which will exhibit LTB4 inhibitory activity in mammals More specifically to produce compounds which inhibit LTB4 activity by acting as inhibitors of PLA₂ enzymes.

The pharmacology of the biologically active leukotrienes is generally discussed in *J. Clin. Invest.* 73, 889–897 (1984).

SUMMARY OF THE INVENTION

This invention relates to compounds of the formula:

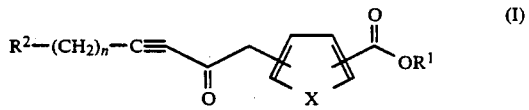

wherein X is oxygen, sulfur or —CH=CH—;
wherein $R^1$ is hydrogen, alkyl of 1 to 6 carbons or a pharmaceutically acceptable cation;
wherein $R^2$ is phenoxy, alkoxy, methyl, trifluoromethyl or phenyl;
wherein n is an integer from 1 to 20.

The present invention also provides pharmaceutical compositions comprised of a therapeutically effective amount of the novel compounds of formula I in combination with a pharmaceutically acceptable carrier and a method for treating inflammatory conditions with said compositions.

DETAILED DESCRIPTION OF THE INVENTION

This invention encompasses compounds of the Formula I as previously described.

Within the class of compounds defined by Formula I, there is a sub-class of preferred compounds represented by Formula II:

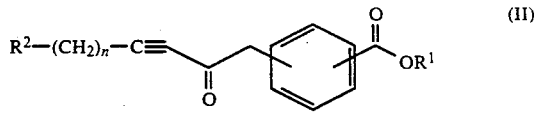

wherein $R^1$ is hydrogen, alkyl of 1 to 6 carbons or a pharmaceutically acceptable cation;
wherein $R^2$ is phenoxy, alkoxy, methyl, trifluoromethyl or phenyl;
wherein n is an integer from 1 to 20.

A preferred class of compounds within Formula II consists of those compounds wherein n is an integer from 8 to 14.

Included within the classes and subclasses of compounds embraced by Formulas I and II are isomeric forms of the described compounds.

The term "pharmaceutically acceptable cation" as used to describe $R^1$ refers to cations such as ammonium, sodium, potassium, lithium, calcium, magnesium, ferrous, zinc, copper, manganous, aluminum, ferric, manganic, tetraalkyl-ammonium and the like. (See for example, S.M. Berge et al., "Pharmaceutical Salts," *J. Pharm. Sci.*, 66:1–19 (1977)). All of the pharmaceutically acceptable cations are prepared by conventional processes which are well known to those of ordinary skill in the art.

The term "composition" as used herein means a product which results from the mixing or combining of more than one element or ingredient.

The term "pharmaceutically-acceptable carrier" as used herein means a pharmaceutically-acceptable material, composition or vehicle, such as a liquid or solid filler, diluent, excipient, solvent or encapsulating material, involved in carrying or transporting a chemical agent from one organ or portion of the body to another organ, or portion of the body. Some examples which can serve as pharmaceutically-acceptable carriers include: (1) sugars, such as lactose, glucose and sucrose; (2) starches, such as corn starch and potato starch; (3) cellulose and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "alkyl" as used herein means a univalent radical having from one to twelve carbon atoms and derived by the removal of a single hydrogen atom from a straight or branched chain saturated hydrocarbon.

Representative of such radicals are methyl, ethyl, n-propyl, isopropyl, n-butyl, sec-butyl, isobutyl, tert-butyl, 2-ethylhexyl, n-octyl, 2,4-dimethylpentyl and the like.

The term "alkoxy" as used herein means an alkyl radical, as defined above, having one or more oxygen atoms attached thereto. Representative alkoxy groups include methoxy, ethoxy, propoxy, tert-butoxy and the like.

The biological activity possessed by the compounds of this invention was indicated by positive results in assays for inhibition of human synovial fluid $PLA_2$ (HSF-$PLA_2$).

By virtue of their activity as $LTB_4$ synthesis inhibitors, the compounds of Formula I are useful in treating inflammatory conditions in mammals such as rheumatoid arthritis, synovitis, bursitis, psoriasis, inflammatory bowel disease and the like. Similarly, the compounds of Formula I can be used in preventing recurring inflammatory attacks. A physician or veterinarian of ordinary skill can readily determine whether a subject exhibits the inflammatory condition. The preferred utility relates to treatment of synovitis, bursitis, rheumatoid arthritis, psoriasis, and inflammatory bowel disease.

The compounds of the present invention can be administered in such oral dosage forms as tablets, capsules, softgels, pills, powders, granules, elixirs, or syrups.

The compounds can also be administered intravascularly, intraperitoneally, subcutaneously, intramuscularly, or topically using forms known to the pharmaceutical art. Moreover, they can be administered rectally or vaginally, in such forms as suppositories or bougies. In general, the preferred form of administration is oral. For the orally administered pharmaceutical compositions and methods of the present invention, the foregoing active ingredients will typically be administered in admixture with suitable pharmaceutical diluents, excipients, or carriers (collectively referred to herein as "carrier" materials) suitably selected with respect to the intended form of administration, that is, oral tablets, capsules, softgels, elixirs, syrups, drops, and the like, and consistent with conventional pharmaceutical practices.

For example, for oral administration in the form of tablets or capsules, a therapeutically effective amount of one or more compounds of the present invention can be combined with any oral non-toxic pharmaceutically acceptable inert carrier such as lactose, starch, sucrose, cellulose, magnesium stearate, dicalcium phosphate, calcium sulfate, mannitol, and the like, or various combinations thereof. For oral administration in liquid forms, such as in softgels, elixirs, syrups, drops and the like, a therapeutically effective amount of the active drug components can be combined with any oral non-toxic pharmaceutically acceptable inert carrier such as water, saline, ethanol, polyethylene glycol, propylene glycol, corn oil, cottonseed oil, peanut oil, sesame oil, benzyl alcohol, various buffers, and the like, or various combinations thereof. Moreover, when desired or necessary, suitable binders, lubricants, disintegrating agents, and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes, or combinations thereof. Lubricants for use in these dosage forms include boric acid, sodium benzoate, sodium acetate, sodium chloride, and the like, or combinations thereof. Disintegrators include, without limitation, starch, methylcellulose, agar, bentonite, guar gum, and the like, or combinations thereof. Sweetening and flavoring agents and preservatives can also be included where appropriate.

For intravascular, intraperitoneal, subcutaneous, or intramuscular administration, one or more compounds of the present invention can be combined with a suitable carrier such as water, saline, aqueous dextrose, and the like. For topical administration, such as for psoriasis, therapeutically effective amounts of one or more compounds of the present invention can be combined with pharmaceutically acceptable creams, oils, waxes, gels and the like.

Regardless of the route of administration selected, the compounds of the present invention are formulated into pharmaceutically acceptable dosage forms by conventional methods known to those skilled in the art. The compounds can also be formulated using pharmacologically acceptable base addition salts. Moreover, the compounds or their salts may be used in a suitable hydrated form.

Regardless of the route of administration selected, a non-toxic but therapeutically effective quantity of one or more compounds of this invention is employed in any treatment. The dosage regimen for preventing or treating inflammatory conditions with the compounds of this invention is selected in accordance with a variety of factors, including the type, age, weight, sex, and medical condition of the patient; the severity of the inflammatory condition, the route of administration, and the particular compound employed in the treatment. A physician or veterinarian of ordinary skill can readily determine and prescribe the effective amount of the drug required to prevent or arrest the progress of the condition. In so proceeding, the physician or veterinarian could employ relatively low doses at first and subsequently increase the dose until a maximum response is obtained. Daily dosages of the compounds of the invention are ordinarily in the range of about 50 to 500 mg, more preferably in the range of about 70 to 300 mg.

The compounds of this invention are generally prepared according to the reaction schemes I and II. As disclosed in Scheme I and II carbobutoxylation of a haloaromatic acetic acid catalyzed by palladium produces the corresponding butyl ester. Transesterification of the butyl ester to the mono methyl ester is achieved by reacting the butyl ester with methanol in the presence of sodium hydride and heating the reaction mixture. The resulting mono methyl ester is treated with oxalyl chloride to afford the ester acid chlorides. The product is then treated with a trimethylsilyl alkyne in the presence of a catalyst ($AlCl_3$) to yield the aromatic acetylenic ketone of formula II.

In scheme I, the aromatic compound is phenyl, thienyl, or furanyl corresponding to the X in the ring being —CH=CH—, —S— or —O—. Halo is defined as halogen corresponding to Br, Cl or I. The trimethylsilylalkyne is represented by TMS-≡-R'. In Scheme II the aromatic compound is 3-bromophenylacetic acid and the trimethylsilyl alkyne is trimethylsilylpentadecyne.

In the structures herein a bond drawn across a bond in a ring indicates that the bond can be to any available carbon atom of the ring structure.

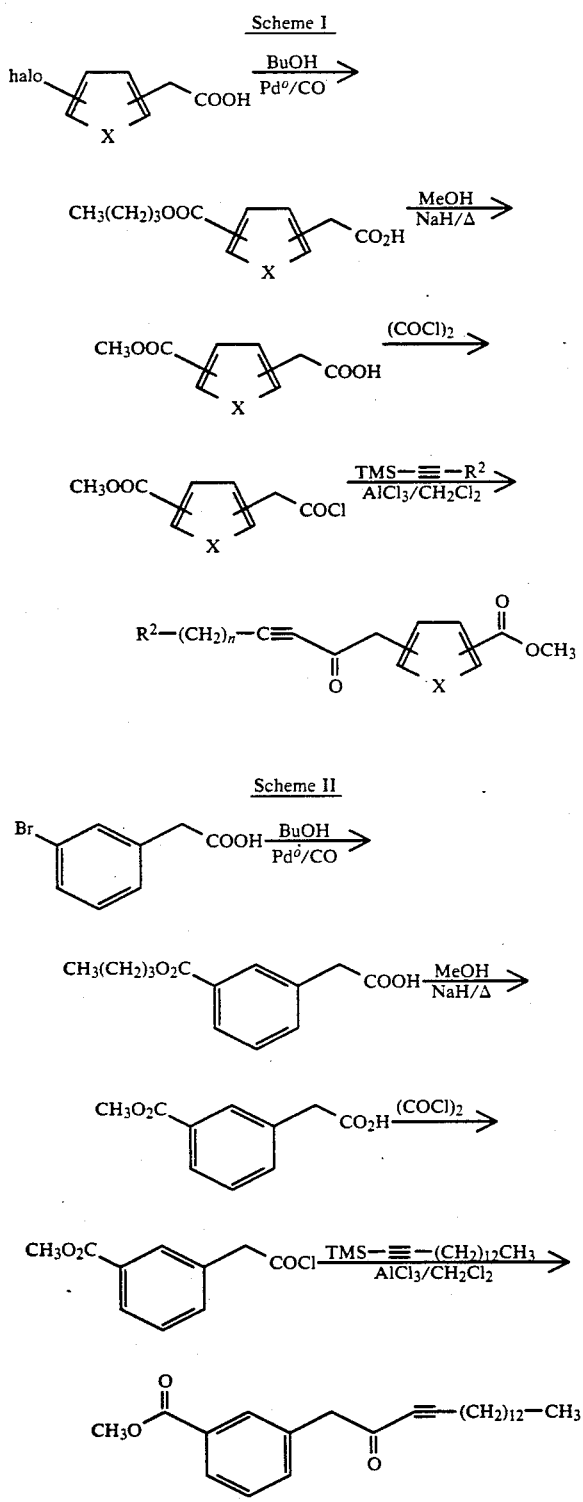

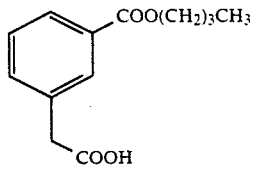

EXAMPLE 1

The above compound was prepared by mixing 14.4 g (66.96 mmoles) of m-bromophenylacetic acid and 2.7 g (3.85 mmoles) of a palladium catalyst [Pd(PPh$_3$)$_2$Cl$_2$] in 75cc of n-butyl alcohol and 75cc of diisopropylamine. The reaction vessel was purged with carbon monoxide. The reaction mixture was heated at 100° C. for 18 hours under a carbon monoxide atmosphere (balloon). The volatile components were removed in vacuo. The residue was taken up in 5% hydrochloric acid and extracted twice with diethyl ether. The extracts were combined and washed once with 5% hydrochloric acid, once with water and dried over magnesium sulfate. The volatile components were removed in vacuo to give a red oil. After chromatography on a silica gel (gradient elution with chloroform/MeOH containing 5% acetic acid), 14.6 g (61.8 mmole) of a waxy solid of the above formula was obtained.

| Analysis: | Carbon | Hydrogen |
|---|---|---|
| found | 66.2 | 6.78 |
| calcd. | 66.09 | 6.83 |

EXAMPLE 2

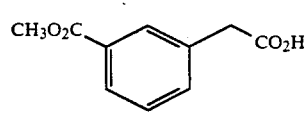

The above compound was produced by adding 14.6 g (61.8 mmoles) of the acid ester produced as in Example 1 to 1 liter methanol and adding 2.9 g (120 mmoles) of sodium hydride portionwise over 15 minutes. The reaction mixture was then heated at reflux for 2 hours. The reaction mixture was cooled to room temperature and poured into 10% hydrochloric acid and extracted twice with ethyl acetate. The extract was washed once with water and dried over magnesium sulfate. A yellow gummy solid resulted which was triturated with cold hexane to yield 8.24 g (42.4 mmoles) of the above product.

EXAMPLE 3

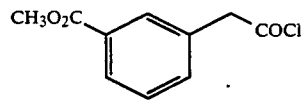

The above compound was prepared by making a solution of 1 g (5.1 mmoles) of the product from Example 2 in 50 cc of benzene and one drop of dimethyl formamide (DMF). To the solution was added 2cc (23.6 mmoles) of oxalyl chloride (COCl)$_2$ over 5 minutes at room temperature. The reaction mixture was stirred for The following examples illustrate the methods used to prepare the compounds of this invention. These examples are given by way of illustration only and are not meant to be construed as limiting the invention in spirit or in scope, as many modifications in materials and methods will be apparent from this disclosure to one having ordinary skill in the art.

2 hours at room temperature. The volatile components were removed in vacuo to yield the above compound.

EXAMPLE 4

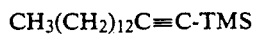

The above compound was prepared by adding an acetylene of the formula CH₃(CH₂)₁₂C≡CH 5g, 23.4 mmoles to 50cc of tetrahydrofuran (THF) and 5mg of triphenylmethane (Ph₃CH) which was added as an indicator. The solution was cooled to −30° C. and 1.6 molar n-butyllithium (n-BuLi) was added dropwise until the solution turned red. Approximately 14.5cc of n-BuLi was added. The solution was back titrated with the acetylene compound until it became colorless. The solution was cooled to −78° C. and 4cc (31.5 mmoles) of trimethylsilyl chloride (TMS-Cll) was added. The solution was slowly warmed over a period of five hours to room temperature. The reaction was quenched with water and extracted with hexane. The extract was washed once with water and once with brine and dried over magnesium sulfate (MgSO₄). The trimethylsilyl alkyne compound above was isolated in an amount of 6.9g (24.6 mmoles).

EXAMPLE 5

Preparation of methyl 3-(2-oxo-3-heptadecynyl) benzoate

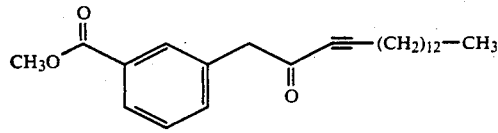

A solution of 1.7g (6 mmole) of the acetylene product of Example 4 and 5.1 mmoles of the acid chloride of Example 3 in 30cc of CH₂Cl₂ was cooled to 0° C. To the solution was added 1.5g (11 mmoles) of AlCl₃ portionwise over 15 minutes. The reaction mixture was stirred for 1 hour at 0° C. The reaction was quenched with ice and then poured into water and extracted twice with diethyl ether. The extracts were combined and washed once with water, once with sodium bicarbonate, once with brine and dried over MgSO₄. The product was chromatographed on silica gel eluted with 5% ether/95%hexane to yield 0.87g of methyl 3-(2-oxo-3-heptadecynyl)benzoate.
HRMS Calcd. 384.2664
HRMS Found 384.2655

EXAMPLE 6

TMS-≡-(CH₂)₉OPh

A solution of 2g (21.2 mmol) phenol and 3.58g (21.2 mmol) 10-undecyn-1-ol and 5.57g (21.2 mmol) of triphenylphosphine and 40cc of tetrahydrofuran was stirred at room temperature under argon. A solution of 3.7g (21.2mmol) of diethyl azodicarboxylate (DEAD) was added dropwise to the reaction mixture at room temperature. The reaction mixture was stirred overnight. The reaction mixture was concentrated, dissolved in ether, filtered and concentrated. This produced 3.5g of an acetylene compound having the following structure.

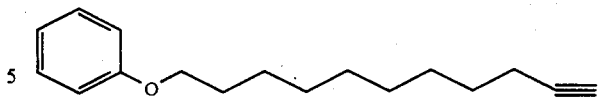

1 g (4.09 mmol) of this acetylene compound was added to 25cc THF and 10mg of triphenyl methane (Ph₃CH) added as an indicator. The reaction mixture was cooled to 30° C. and 1.6M n-butyllithium was added dropwise until the solution turned red. The solution was back titrated with the acetylene compound until it became colorless. The solution was then cooled to −78° C. and 2cc (15.8 mmoles) of trimethylsilyl chloride was added. The solution was slowly warmed over a period of 5 hours to room temperature. The reaction was quenched with water and extracted with hexane. The hexane was washed once with water, once with brine and dried over magnesium sulfate. The trimethylsilyl acetylene was isolated in an amount of 1.26g (3.98 mmoles).

EXAMPLE 7

Preparation of methyl 3-(2-oxo-13-phenoxy-3-tridecynyl)benzoate

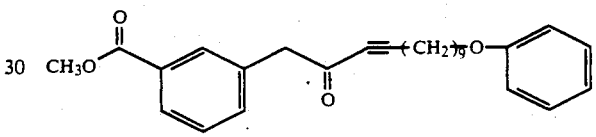

The above compound was prepared by converting 0.3 g (1.54 mmol) of the acid ester of Example 2 to the ester chloride of Example 3 by the methodology of Example 3. The ester chloride product was mixed in a solution of 5cc CH₂Cl₂ with 0.63g (2 mmol) of the trimethylsilyl acetylene of Example 6. The solution was cooled to 0° C. and 0.4g (3 mmole) AlCl₃ was added portionwise over 15 minutes. The reaction mixture was stirred for 1 hour at 0° C. The reaction was quenched with ice and then poured into water and extracted twice with diethyl ether. The extracts were washed once with water, once with sodium bicarbonate, once with brine and dried over magnesium sulfate. The resulting product was chromatographed on silica (gradient elution with ether/hexane) to yield 0.051g of the above compound.
HRMS Calcd. 420.2300
HRMS Found 420.2310

EXAMPLE 8

CH₃O—(CH₂)₉—≡—TMS

The above compound was prepared by cooling a solution of 1 g (5.94 mmol) hydroxyacetylene of the formula HO—(CH₂)₉—≡CH in 10cc of THF to 0° C. Methyl iodide in the amount of 1 cc (16.1 mole) was added to the solution followed by the portionwise addition of 0.2 g of sodium hydride. The reaction mixture was stirred and warmed to room temperature overnight. The solution was poured into 100 cc water and extracted with hexane. The extract was washed once with water and once with brine and dried over magnesium sulfate. Removal of the solvent yielded 1.21 g (6.6 mmole) of a pale yellow oil of the formula CH₃O—(CH₂)₉—≡—H. 1 g (5.5 mmole) of this acetylene was added to 25 cc THF and 10 mg of triphenylmethane added as an indicator. The solution was cooled to 0° C. and 1.6M n-butyl lithium in hexane was added. Approximately 3.4 cc n-butyl lithium was added. The solution was back titrated with the acetylene until colorless. The solution was then cooled to −78° C. and 2 cc (15. 8 mmole) of trimethylsilylchloride was added. The solution was slowly warmed to room temperature over a period of 5 hours. The reaction was quenched with water and extracted with hexane. The extract was washed once with water and once with brine and dried over magnesium sulfate. The trimethylsilyl acetylene was isolated in an amount of 1.26 g (4.95 mmols).

EXAMPLE 9

Preparation of methyl 3-(2-oxo-13-methoxy-3-tridecynyl)benzoate

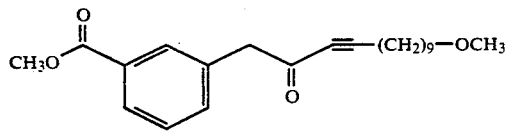

The above compound was prepared by first converting 0.3 g (1.54 mmol) of the ester acid of Example 1 to the ester chloride of Example 3 by the methodology of example 3. The resulting product was reacted with 0.51g (2 mmole) of the TMS acetylene of Example 8 in 5 cc of CH$_2$Cl$_2$. The solution was cooled to 0° C. and 0.40g (3 mmole) of AlCl$_3$ was added portionwise over 15 minutes. The reaction mixture was stirred for 1 hour at 0° C., quenched with ice and poured into water. The solution was extracted twice with diethyl ether. The extracts were combined, washed once with water, once with sodium bicarbonate, once with brine and dried over magnesium sulfate. The product was chromatographed on silica gel (gradient eluted with diethyl ether/hexane) to yield 0.035g of 3-(2-oxo-13-methoxy-3-tridecynyl)benzoate.

HRMS Calcd. 358.2144
HRMS Found 358.2149

EXAMPLE 10

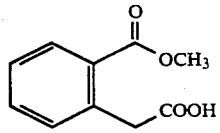

A solution of 5 g of 2-carboxyphenylacetic acid, 1 cc of sulfuric acid and 20 cc of methanol was stirred at room temperature overnight. The solution was neutralized with 10% sodium hydroxide (NaOH) and worked up with ethyl acetate/hexane. This yielded methyl 2-(methoxycarbonyl) phenylacetate. A solution of 3.3 g of this compound, 3.5 g potassium carbonate (K$_2$CO$_3$), 35 cc ethanol and 35 cc water was stirred at 100° C. under reflux for 4 hours. The reaction mixture was washed with ethyl acetate and water. The product was recrystallized from hexane and ethyl acetate. This afforded the above product.

EXAMPLE 11

Preparation of methyl 2-(2-oxo-3heptadecynyl)benzoate

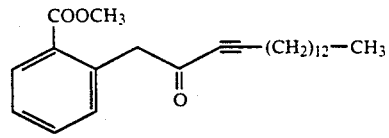

To prepare the above compound 0.3 g of the product from example 10 was mixed in 50 cc of benzene. To the solution was added 2 cc of oxalyl chloride (COCl)$_2$ dropwise over 5 minutes at room temperature. The reaction mixture was stirred for 2 hours at room temperature. The volatile components were removed in vacuo to yield the ester acid chloride. 0.56 g of the trimethylsilyl acetylene of Example 4 was added to the product in a solution of 5 cc of CH$_2$Cl$_2$. The solution was cooled to 0° C. and 0.4 g AlCl$_3$ was added portionwise over 15 minutes. The reaction mixture was stirred for 1 hour at 0° C. The reaction was quenched with ice and then poured into water. The solution was extracted twice with diethyl ether. The extracts were combined, washed once with water, once with sodium bicarbonate, once with brine and dried over magnesium sulfate. The product was chromatographed on silica gel (gradient elution with ether/hexane) to yield 0.37 g of the above product.

HRMS Calcd. 384.2664
HRMS Found 384.2661

EXAMPLE 12

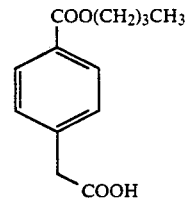

The above compound was prepared by mixing 4 g (15.3 mmoles) p-iodoacetic acid and 25 cc n-butylalcohol with 0.5 g (0.71 mmole) of a palladium catalyst Pd(PPh$_3$)$_2$Cl$_2$ in 25 cc of diisopropyl amine. The reaction mixture was purged with carbon monoxide and heated at 80° C. for 18 hours under a carbon monoxide atmosphere (balloon). The volatile components were removed in vacuo and the residue taken up in 5% hydrochloric acid. The solution was extracted twice with diethyl ether. The extract was washed once with 5% hydrochloric acid, once with water and dried over magnesium sulfate. The volatile components were removed in vacuo to give a red oil. The product was chromatographed on silica gel (gradient elution with chloroform/methanol containing 5% acetic acid) to yield 1.9 g (8.04 mmole) of the acid ester of the above formula.

EXAMPLE 13

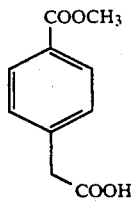

A solution of 1.9 g (8.04 mmole) of the acid ester of Example 12 in 100 cc methanol was treated with 1.0 g (20.8 mmole) sodium hydride (50% in oil) portionwise over 15 minutes. The reaction mixture was heated and refluxed for 2 hours. The reaction mixture was cooled to room temperature and poured into 10% hydrochloric acid. The solution was extracted twice with ethyl acetate. The extracts were combined, washed once with water and dried over magnesium sulfate. A yellow solid was obtained which was triturated with cold hexane to obtain the above compound.

EXAMPLE 14

Preparation of methyl 4-(2-oxo-3heptadecynyl)benzoate

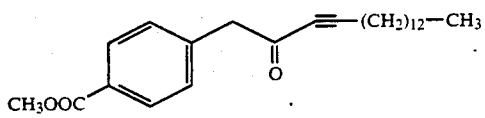

A solution was made by adding 0.3 g (1.54 mmole) of the product from example 13 to 10 cc benzene. To the solution was added 1 cc (11.8 mmoles) of oxalyl chloride (COCl)$_2$ dropwise over 15 minutes at room temperature. The reaction mixture was stirred for 2 hours at room temperature. The volatile components were removed in vacuo to yield the ester acid chloride.

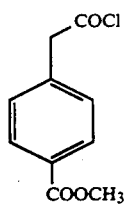

This compound was mixed in 5 cc of CH$_2$Cl$_2$ with 0.56 g (2 mmole) of the trimethylsilyl acetylene of Example 4. The solution was cooled to 0° C. and 0.4 g (3 mmole) of AlCl$_3$ was added portionwise over 15 minutes. The solution was stirred for 1 hour at 0° C. and quenched with ice. The solution was poured into water and extracted twice with diethyl ether. The extracts were combined and washed once with water, once with sodium bicarbonate, once with brine and dried over magnesium sulfate. The product was chromatographed on a silica gel (gradient elution with ether/hexane) to yield 0.25 g of methyl 4-(2-oxo-3-heptadecynyl)benzoate.

HRMS Calcd. 384.2664
HRMS Found 384.2660

EXAMPLE 15

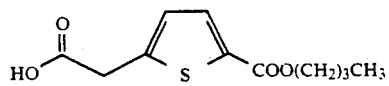

The above compound is prepared by mixing 3.4 g (15.3 mmoles) 5-bromo-2-thiopheneacetic acid (Ref. U.S. Pat. No. 2,425,721) and 25 cc n-butyl-alcohol with 0.5 g (0.71 mmole) of a palladium catalyst Pd(PPh$_3$)$_2$Cl$_2$ in 25 cc of diisopropyl amine. The reaction mixture is purged with carbon monoxide and heated at 80° C. for 18 hours under a carbon monoxide atmosphere (balloon). The volatile components are removed in vacuo and the residue taken up in 5% hydrochloric acid. The solution is extracted twice with diethyl ether. The extract is washed once with 5% hydrochloric acid, once with water and dried over magnesium sulfate. The volatile components are removed in vacuo to give the crude product. The product is chromatographed on silica gel to yield the acid ester of the above formula.

EXAMPLE 16

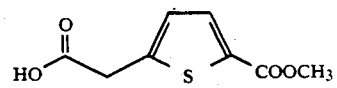

A solution of 1.95 g (8.04 mmole) of the acid ester of Example 15 in 100 cc methanol is treated with 1.0 g (20.8 mmole) sodium hydride (50% in oil) portionwise over 15 minutes. The reaction mixture is heated and refluxed for 2 hours. The reaction mixture is cooled to room temperature and poured into 10% hydrochloric acid. The solution is extracted twice with ethyl acetate. The extracts are combined, washed once with water and dried over magnesium sulfate. After removal of the solvent in vacuo, the above compound is obtained.

EXAMPLE 17

Preparation of methyl 5-(2-oxo-3-heptadecynyl)-2-thiophenecarboxylate

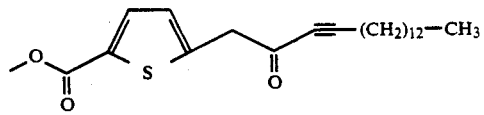

A solution is made by adding 0.31 g (1.54 mmole) of the product from example 16 to 10 cc benzene. To the solution is added 1 cc (11.8 mmoles) of oxalyl chloride (COCl)$_2$ dropwise over 15 minutes at room temperature. The reaction mixture is stirred for 2 hours at room temperature. The volatile components are removed in vacuo to yield the ester acid chloride.

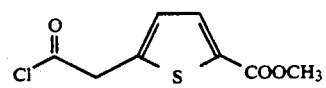

This compound is mixed in 5 cc of CH$_2$Cl$_2$ with 0.56 g (2 mmole) of the trimethylsilyl acetylene of Example 4. The solution is cooled to 0° C. and 0.4 g (3 mmole) of AlCl3 is added portionwise over 15 minutes. The solution is stirred for 1 hour at 0° C. and quenched with ice. The solution is poured into water and extracted twice with diethyl ether. The extracts are combined and washed once with water, once with sodium bicarbonate, once with brine and dried over magnesium sulfate. The product is chromatographed on a silica gel to yield methyl 5-(2-oxo-3-heptadecynyl)-2-thiophene-carboxylate.

EXAMPLE 18

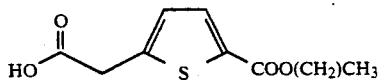

The above compound is prepared by mixing 3.1 g (15.3 mmoles) 5-bromo-2-furanacetic acid (Ref: as in U.S. Pat. No. 2,425,721 for thiophene analogue) and 25 cc n-butyl-alcohol with 0.5 g (0.71 mmole) of a palladium catalyst Pd(PPh3)2Cl2 in 25 cc of diisopropyl amine. The reaction mixture is purged with carbon monoxide and heated at 80° C. for 18 hours under a carbon monoxide atmosphere (balloon). The volatile components are removed in vacuo and the residue taken up in 5% hydrochloric acid. The solution is extracted twice with diethyl ether. The extract is washed once with 5% hydrochloric acid, once with water and dried over magnesium sulfate. The volatile components are removed in vacuo to give the crude product. The product is chromatographed on silica gel to yield the acid ester of the above formula.

EXAMPLE 19

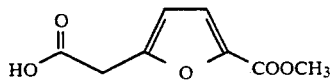

A solution of 1.8 g (8.04 mmole) of the acid ester of Example 18 in 100 cc methanol is treated with 1.0 g (20.8 mmole) sodium hydride (50% in oil) portionwise over 15 minutes. The reaction mixture is heated and refluxed for 2 hours. The reaction mixture is cooled to room temperature and poured into 10% hydrochloric acid. The solution is extracted twice with ethyl acetate. The extracts are combined, washed once with water and dried over magnesium sulfate. After removal of the solvent in vacuo, the above compound is obtained.

EXAMPLE 20

Preparation of methyl 5-(2-oxo-3-heptadecynyl)-2-furancarboxylate

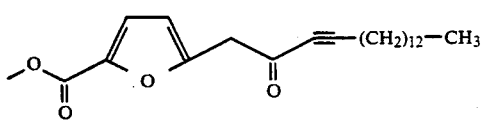

A solution is made by adding 0.28 g (1.54 mmole) of the product from example 19 to 10 cc benzene. To the solution is added 1 cc (11.8 mmoles) of oxalyl chloride (COCl)2 dropwise over 15 minutes at room temperature. The reaction mixture is stirred for 2 hours at room temperature. The volatile components are removed in vacuo to yield the ester acid chloride.

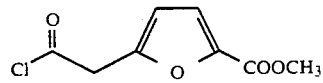

This compound is mixed in 5 cc of CH2Cl2 with 0.56 g (2 mmole) of the trimethylsilyl acetylene of Example 4. The solution is cooled to 0° C. and 0.4 g (3 mmole) of AlCl3 is added portionwise over 15 minutes. The solution is stirred for 1 hour at 0° C. and quenched with ice. The solution is poured into water and extracted twice with diethyl ether. The extracts are combined and washed once with water, once with sodium bicarbonate, once with brine and dried over magnesium sulfate. The product is chromatographed on a silica gel to yield methyl 5-(2-oxo-3-heptadecynyl)-2-furancarboxylate.

HUMAN SYNOVIAL FLUID PHOSPHOLIPASE A2 (HSF-PLA2) ASSAY

Human synovial fluid phospholipase A2 was purified approximately 5000 fold following the procedures of Franson et al., Lung 160, 275-284 (1982) and Vishwanath et al., Inflammation 12(6), 549-56 (1988). Following purification the enzyme activity was measured by a modified methodology using [$^{14}$C]-oleate-labeled, autoclaved E. coli as the substrate as also shown in the above noted references. The assay was performed in a final volume of 100 μl containing 50 mM HEPES (pH 7.0), 150 mM NaCl, 5mM CaCl2, 7 n mole [$^{14}$C]-oleate-labeled E. coli phospholipid and with or without the compound from one of the examples herein undergoing an assay. The compound or control vehicle was pre-incubated with the PLA2 for 5 minutes followed by addition of the E. coli substrate to initiate the reaction. The reaction was maintained at 37° C. for 30 minutes and then terminated by the addition of 2 ml tetrahydrofuran (THF). The reaction product, [$^{14}$C]-oleic acid, was extracted using a 1 ml Bond Elut-NH2 Solid phase extraction column. The IC50 value for the compound (mean −S.E.) is given in the following Table I and represents the concentration of the indicated compound required to inhibit 50% of the PLA2 activity.

TABLE I

| HUMAN SYNOVIAL FLUID PLA2 ASSAY TEST RESULTS | |
| --- | --- |
| Example # | HSF-PLA2 IC50(μM) |
| 5 | 6.0 |
| 7 | 2.75 |
| 9 | 20.6 |
| 11 | 17.4 |
| 14 | 2.2 |

What is claimed is:
1. A compound of the formula

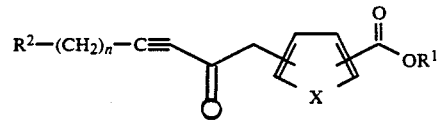

wherein X is oxygen, sulfur or —CH═CH—;
wherein R$^1$ is hydrogen, alkyl of 1 to 6 carbons or a pharmaceutically acceptable cation;
wherein R$^2$ is phenoxy, trifluoromethyl, phenyl, alkoxy or methyl; and
wherein n is an integer from 1 to 20.

2. A compound according to claim 1 wherein X is —CH=CH—.

3. A compound according to claim 2 wherein $R^2$ is methyl, phenoxy or alkoxy.

4. A compound according to claim 3 wherein $R^2$ is methyl.

5. A compound according to claim 4 which is methyl 4-(2-oxo-3-heptadecynyl)benzoate.

6. A compound according to claim 4 which is methyl 2-(2-oxo-3-heptadecynyl)benzoate.

7. A compound according to claim 4 which is methyl 3-(2-oxo-3-heptadecynyl)benzoate.

8. A compound according to claim 3 wherein $R^2$ is alkoxy.

9. A compound according to claim 8 which is methyl 3-(2-oxo-13-methoxy-3-tridecynyl)benzoate.

10. A compound according to claim 3 wherein $R^2$ is phenoxy.

11. A compound according to claim 10 which is methyl 3-(2-oxo-13-phenoxy-3-tridecynyl)benzoate.

12. A compound according to claim 1 wherein X is oxygen.

13. A compound according to claim 12 wherein $R^2$ is methyl.

14. A compound according to claim 12 wherein $R^2$ is a phenoxy.

15. A compound according to claim 12 wherein $R^2$ is alkoxy.

16. A compound according to claim 1 wherein X is sulfur.

17. A compound according to claim 16 wherein $R^2$ is methyl.

18. A compound according to claim 16 wherein $R^2$ is phenoxy.

19. A compound according to claim 16 wherein $R^2$ is alkoxy.

20. A pharmaceutical composition comprising a therapeutically effective amount of a compound according to claim 1 and a pharmaceutically acceptable carrier.

21. A method of treating inflammatory conditions in mammals comprising administering to a patient in need of such treatment, a therapeutically effective amount of a composition according to claim 20.

* * * * *

UNITED STATES PATENT AND TRADEMARK OFFICE
CERTIFICATE OF CORRECTION

PATENT NO. : 5,112,864

DATED : May 12, 1992

INVENTOR(S) : Stevan Wakefield Djuric, et al.

It is certified that error appears in the above-identified patent and that said Letters Patent is hereby corrected as shown below:

Column 1, line 5, reading "1. Field of the Invention" should read -- Field of the Invention --

Column 1, line 42, reading "activity in mammals" should read --activity in mammals. --

Column 7, line 17, reading "(TMS-C11)" should read -- (TMS-Cl) --

Column 8, line 54, reading "$CH_3O-(CH_2)_9$-b-TMS" should read -- $CH_3O-(CH_2)_9-\equiv-TMS$ --

Column 10, line 3, reading "2-(2-oxo-3heptadecynyl)" should read -- 2-(2-oxo-3-heptadecynyl) --

Column 11, line 27, reading "4-(2-oxo-3heptadecynyl)" should read -- 4-(2-oxo-3-heptadecynyl) --

Column 13 Example 18 structure reading

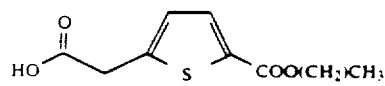   should read   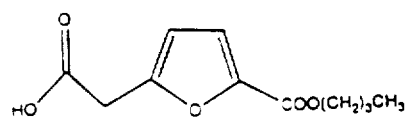

UNITED STATES PATENT AND TRADEMARK OFFICE
CERTIFICATE OF CORRECTION

PATENT NO. : 5,112,864

DATED : May 30, 1991

INVENTOR(S) : Stevan Wakefield Djuric, et al.

It is certified that error appears in the above-identified patent and that said Letters Patent is hereby corrected as shown below:

Column 14, line 42, reading "(mean - S.E.)" should read -- (mean +/- S.E.) --

Signed and Sealed this

Seventh Day of September, 1993

Attest:

BRUCE LEHMAN

Attesting Officer

Commissioner of Patents and Trademarks